United States Patent
Martínez

(10) Patent No.: US 9,107,341 B2
(45) Date of Patent: Aug. 18, 2015

(54) MONITORING AND CONTROL OF SOIL CONDITIONS

(71) Applicant: Labs & Technological Holding Solea, S.L., Seville (ES)

(72) Inventor: Estanislao Martínez Martínez, Oxnard, CA (US)

(73) Assignee: AGQ TECHNOLOGICAL CORPORATE S.A., Seville (ES)

( * ) Notice: Subject to any disclaimer, the term of this patent is extended or adjusted under 35 U.S.C. 154(b) by 43 days.

(21) Appl. No.: 13/654,769

(22) Filed: Oct. 18, 2012

(65) Prior Publication Data

US 2013/0226347 A1   Aug. 29, 2013

Related U.S. Application Data

(60) Provisional application No. 61/603,608, filed on Feb. 27, 2012.

(51) Int. Cl.
*G05D 11/00* (2006.01)
*A01C 21/00* (2006.01)
(Continued)

(52) U.S. Cl.
CPC ............ *A01C 21/007* (2013.01); *G05D 11/138* (2013.01); *G01N 1/14* (2013.01); *G01N 2033/245* (2013.01)

(58) Field of Classification Search
CPC ... G01N 1/14; G01N 2033/245; G05D 11/00; G05D 11/138; A01C 17/006; A01C 21/007; A01C 21/00
USPC ................... 700/266, 284; 702/22, 23, 30–31
See application file for complete search history.

(56) References Cited

U.S. PATENT DOCUMENTS 5,375,478 A   12/1994   Bernhardt
5,668,719 A    9/1997   Bobrov et al.
(Continued)

FOREIGN PATENT DOCUMENTS

WO   WO2004071162       8/2004
WO     2008/149361 A2   12/2008

OTHER PUBLICATIONS

International Search Report and WO for co-pending PCT application No. PCT/US2012/060764, Mar. 26, 2013.
(Continued)

*Primary Examiner* — Shogo Sasaki
(74) *Attorney, Agent, or Firm* — Thomas | Horstemeyer, LLP

(57) ABSTRACT

Various methods and systems are provided for monitoring and control of soil conditions. In one example, among others, a method includes obtaining aqueous samples from suction probes within a soil substrate and analyzing the aqueous samples to determine a chemical composition of the soil substrate. Amounts of an additive may be determined to adjust the chemical composition of the soil substrate. In another example, a method includes installing a suction probe within a soil substrate; drawing a vacuum to induce hydraulic conduction of aqueous solutions from the soil substrate; extracting an aqueous sample; and analyzing the aqueous sample to determine a chemical composition of the soil substrate. In another example, a method includes obtaining a composition of a fertilizer solution (FS) supplied to a soil substrate and a chemical composition within the soil substrate; determining nutrient utilization, and providing an amount of additive to produce a subsequent FS for supply.

32 Claims, 6 Drawing Sheets

(51) Int. Cl.
*G05D 11/13* (2006.01)
*G01N 1/14* (2006.01)
*G01N 33/24* (2006.01)

(56) References Cited

U.S. PATENT DOCUMENTS

| | | |
|---|---|---|
| 5,887,491 A | 3/1999 | Monson et al. |
| 6,852,286 B2 | 2/2005 | Martinez |
| 2006/0178847 A1 | 8/2006 | Glancy et al. |
| 2006/0254138 A1 | 11/2006 | Bissonnette et al. |
| 2006/0254371 A1* | 11/2006 | Shiloni et al. .............. 73/864.34 |
| 2010/0332039 A1 | 12/2010 | Danieli |

OTHER PUBLICATIONS

Dossier, AGQ Agrofood & Environment, Labs & Technological Services (Jul. 2010) www.agq.com.es.

Dossier, AGQ Agrofood & Environment, Labs & Technological Services (Jul. 2011) www.agq.com.es.

International Search Report and WO for co-pending PCT application No. PCT/IB2012/002718, Apr. 29, 2013.

* cited by examiner

|  | Effect in the plant | | | | | | | | | | | | |
|---|---|---|---|---|---|---|---|---|---|---|---|---|---|
|  | N | P | K | Ca | Mg | S | Fe | Mn | Zn | Cu | B | Cl | Mo |
| N | + |  | − | + |  | − |  |  |  |  | − |  |  |
| P |  | + | − | + |  |  |  |  | − | − | − | − | + |
| K |  |  | + | − | − |  |  |  |  |  |  |  |  |
| Ca |  |  | − | + | − |  |  | − |  |  |  |  |  |
| Mg |  | + | − | − | + |  |  | − | − |  |  |  |  |
| S |  | − |  |  |  | + |  |  |  |  |  | − | − |
| Fe |  |  |  |  |  |  | + | − |  | − |  |  |  |
| Mn |  |  |  | − |  |  | − | + | − |  |  |  |  |
| Zn |  | − |  |  |  |  |  |  | + |  |  |  |  |
| Cu |  |  |  |  |  |  | − | − | − | + |  |  | − |
| B |  |  |  |  |  |  |  |  | − |  | + |  |  |
| Cl |  |  |  |  |  | − |  |  | + |  |  | + |  |
| Mo |  |  |  |  |  |  |  |  |  | − |  |  | + |

FIG. 5

MONITORING AND CONTROL OF SOIL CONDITIONS

CROSS REFERENCE TO RELATED APPLICATIONS

This application claims priority to U.S. provisional application entitled "MONITORING AND CONTROL OF SOIL CONDITIONS" having Ser. No. 61/603,680, filed Feb. 27, 2012, which is hereby incorporated by reference in its entirety.

BACKGROUND

As population continues to increase, food production becomes an ever expanding problem. Effective use of water resources affects the productivity of agricultural farms. In addition, fertilization has become one of the main factors enhancing productivity and quality of agricultural farms. This has resulted in increased consumption of fertilizers worldwide, raising new issues such as increased production costs and contamination effects from agricultural activity.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 5 is a table illustrating the relationship between various additives and their effect in a plant according to various embodiments of the present disclosure.

DETAILED DESCRIPTION

Figure 1:
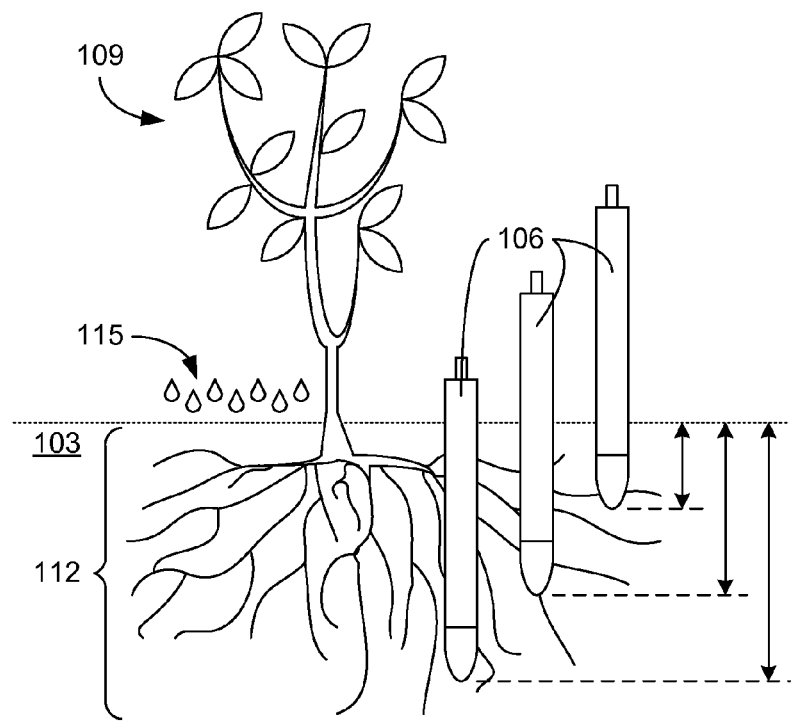
FIG. 1 is a graphical representation illustrating the monitoring of the condition of the soil using a plurality of suction probes according to various embodiments of the present disclosure.

Disclosed herein are various embodiments related to monitoring and control of soil conditions in, e.g., agricultural applications. Reference will now be made in detail to the description of the embodiments as illustrated in the drawings, wherein like reference numbers indicate like parts throughout the several views.

Controlled application of water and fertilizers can enhance the productivity of agricultural farms in a sustainable fashion, providing greater profitability, food safety, and environmental preservation. Monitoring the nutritional conditions of the crops may be used to control the application of available resources (e.g., water and fertilizer) to fulfill the plants nutritional needs throughout their evolution; thereby improving productivity and quality of the resulting produce while reducing inputs and loss through lixiviation.

Analysis of the chemical composition of the soil and/or liquids about the roots of the plants, as well as diagnosis of the plant condition, can provide an indication of nutrient absorption by the plants which may be used to control watering and/or fertilization. Monitoring of the soil condition may be accomplished using suction probes installed at different depth levels of the root profiles of the crops. By extracting aqueous solutions from the soil substrate about the roots, the interaction of the root activity and soil conditions may be monitored and used to control the application of nutrients to the soil substrate. For example, the reaction and behavior of the inputs (e.g., water, effluents, fertilizers, coadyuvants, chelates, etc.) added to the soil and the reaction of the soil to these inputs, as well as root activity for nutrient absorption, may be evaluated throughout the phenological cycle of the plants to provide indications that may be used for controlling the application of additives such as, e.g., chemical nutrients in a cyclic or continuous manner.

Referring to FIG. 1, shown is a graphical representation illustrating the monitoring of the condition of the soil 103 using one or more suction probes 106 according to various embodiments of the present disclosure. For example, plants 109 of the same species are planted in the soil substrate 103 with their roots extending through a root activity zone 112. Water and/or fertilizer solutions 115 may be provided to the plants 109 through drip lines, sprinklers, or other delivery system. In the example of FIG. 1, suction probes 106 are located at a plurality of depths (or levels) within the root activity zone 112 of the plant(s) 109. For example, suction probes 106 may be placed at two depths (e.g., about 15 cm and about 30 cm) for vegetable crops or three depths (e.g., about 20 cm, about 40 cm, and about 60 cm) for woody plants. Suction probes 106 may also be located at other depths as can be understood. The depth(s) may vary based upon the plant species. In addition, probes may be installed at a depth below the root activity zone 112 to monitor for propagation of unused nutrients through the root activity zone 112. Additional suction probes 106 at the same or different depths may also be utilized. For instance, suction probes 106 may be distributed, either individually or in groups, at different locations within a row, bed, and/or field to monitor for variations within the field.

In other implementations, one or more suction probes 106 may be placed at one or more depths in the soil substrate 103 for environmental monitoring such as, e.g., where lixiviation is monitored. For example, in the metal or mining industries where washes and flushing are often used, monitoring for metal or other contamination in the soil substrate 103 may be implemented using suction probes 106. Possible applications may include, but are not limited to, static leaching, site monitoring for decontamination, medium and long term monitoring of restoration and/or rehabilitation of affected spaces, leakage and/or spoilage monitoring, etc. using one or more suction probes to obtains samples from a soil substrate. Aqueous samples may be analyzed for chemical composition to monitor for variations in the soil substrate 103. Remedial or corrective actions may be taken based upon the monitored sample composition. Analysis of the samples may be used to provide warnings and/or alarms and/or to propose corrective measures to eliminate or reduce the environmental effects.

Figure 2:
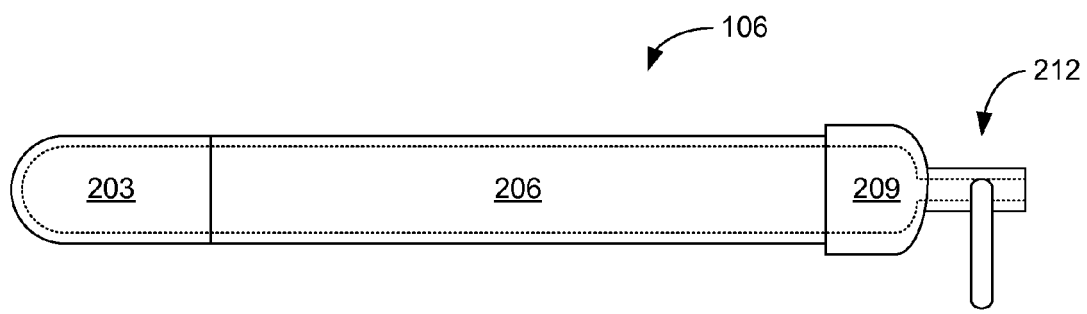
FIG. 2 is a graphical representation of an example a suction probe of FIG. 1 according to various embodiments of the present disclosure.

FIG. 2 illustrates an example a suction probe 106 of FIG. 1. The suction probe 106 of FIG. 2 includes a porous capsule 203 of, e.g., porcelain attached to one end of a tube 206 of inert material such as, e.g., hard rubber, polyethylene, or PVC. For example, the porous capsule 203 may be about 50 mm in diameter and extend from the end of the tube by about 85 mm. The porous porcelain may have a thickness of about 5 mm with a porosity of about 25-23% and an average porous diameter of about 8-10 Å. Other chemically inert materials may also be used for the porous capsule 203 such as, e.g., porous ceramic. The porous characteristics of the material used in the porous capsule 203 allow for hydraulic conductivity of aqueous solutions from the soil when a vacuum is drawn inside the suction probe 106. The porosity of the porous capsule 203 should allow the monitored chemical composition to enter the suction probe 106 without difficulty. In addition, other shapes and dimensions may also be used for the porous capsule 203 and/or suction probe 106. A cap 209 (e.g., rubber or PVC) seals the opposite end of the tube 206. A fitting 212 attached to the cap 209 allows for connection to a vacuum pump to draw a vacuum within the hollow suction probe 106. The fitting 212 may include a valve to allow the vacuum pump to be disconnected while maintaining the vacuum within the suction probe 106.

Referring back to FIG. 1, the suction probes 106 are installed in a vertical position within the soil 103 at a plurality of depths within the root activity zone 112. For example, a hole may be drilled into the soil 103 and the suction probe 106 may be inserted to the appropriate depth. In general, a group of suction probes 106 are installed in an area of good root activity under the same plant or under neighboring plants that are in the same phenological stage. For example, a group of suction probes may be installed along a crop row of plants that were planted together. The location of the suction probes 106 may also take into account the position of the irrigation system. For instance, a suction probe 106 may be located in the center of a wet area under a drip line. Also, suction probes 106 should be adequately spaced apart (e.g., about 20-30 cm) to allow room for adequate sampling of aqueous solutions from the surrounding soil without competing with an adjacent suction probe 106.

In some implementations, the porous capsules 203 (FIG. 2) of the suction probes 106 may be submerged in water (e.g., for about 15-20 minutes) to allow for hydration of the porous capsules 203. Hydration of the porous capsules 203 can improve the hydraulic connection between the soil 103 and the porous capsules 203. Hydration may also facilitate insertion of the suction probe 106 into the soil 103. The surrounding soil 103 may also be packed around the suction probe 106 (e.g., using a wire) to ensure a good hydraulic connection between the porous capsule 203 and the soil 103. Samples of the soil 103 at various depths (e.g., 0-30 cm and 30-60 cm) may be obtained during installation of the suction probes 106. A soil sample may be obtained for each of the probe depths. A soil sampling protocol may be followed to ensure that the samples represent a true indication of the soil composition. Analysis of the soil samples can provide base line information about the composition of the soil substrate 103.

After installation of the suction probes 106, aqueous solutions may be extracted from the substrate surrounding the roots of the plant(s) by drawing a vacuum in the suction probes 106. A vacuum pump (not shown) may be connected to the fitting 212 (FIG. 2) to draw a vacuum within a hollow suction probe 106. For example, the vacuum may be in the range of about 0.5 atmosphere (atm) to about 1.0 atm, in the range of about 0.6 atm to about 0.9 atm, in the range of about 0.7 atm to about 0.8 atm, or about 0.8 atm. A meter may be used to indicate the vacuum within the suction probe 106. Once the vacuum has been drawn within the suction probe 106, a valve included in fitting 212 may be closed to maintain the vacuum in the suction probe 106. In some cases, the size of the suction probe 106 may allow a vacuum to be drawn with a manual pump.

The vacuum within a suction probe 106 hydraulically conducts an aqueous solution from the surrounding soil 103 into the suction probe 106 through the porous capsule 203 (FIG. 2). The volume of the collected solution will depend on the hydraulic conductivity of the soil substrate 103 and the water content of the soil 103, as well as the extraction time during which the vacuum is maintained in the suction probe 106. For example, the extraction period may be about 2 days to about 4 days. Vacuum conditions and air tightness depends upon porous characteristics of the material of the porous capsule 203 and the connection with the surrounding soil 103. In some implementations, the vacuum may be maintained within a range of values over the extraction period.

At the end of the extraction period (e.g., after about 48 hours), an aqueous sample is collected from the suction probe 106. An aqueous sampling protocol may be followed to ensure that the samples represent a true indication of the chemical composition of the aqueous sample. For example, the aqueous sample may be obtained through a micro tube that passes through the open fitting 212 (FIG. 2) to the porous capsule at the end of the suction probe 106. A syringe (or other extraction device) may be used to extract the aqueous sample from the suction probe 106 through the micro tube. Aqueous samples of 30 ml or more may be obtained and provided for analysis. In some implementations, a 125 ml aqueous sample is obtained. In some embodiments, a separate sampling tube is provided for obtaining aqueous samples through the cap 209 (FIG. 2) of the suction probe 106. The sampling tube may pass through a separate hermetically sealed opening in the cap 209. A valve in the sampling tube may be used to close off the sampling tube during the extraction period. The valve may then be opened to allow the aqueous sample to be obtained from the suction probe 106. The aqueous samples from the suction probe 106 may then be provided for chemical analysis and further evaluation.

In addition to the aqueous samples from the suction probe 106, samples of a fertilizer solution (FS) 115 (FIG. 1) that is supplied to the plants 109 may be obtained during irrigation of the plants 109 (FIG. 1). The FS 115 includes irrigation water that may be mixed with additives such as, e.g., fresh or filtered water, residue water, fertilizers, minerals, chemicals and/or other nutrients. A sampling protocol may be followed to ensure that the samples represent a true indication of the FS composition. For example, one or more collection device(s) located in the vicinity of the suction probes 106 collect FS 115 during plant irrigation. A plurality of collection devices may be distributed at different locations within a row, bed, and/or field to monitor for variations in distribution of the FS 115 within the field. In the case of drip irrigation, a collection device such as, e.g., an appropriately sized liquid container may receive FS 115 from the drip line through an adapter near the group of suction probes 106 (FIG. 1). Thus, when the plants 109 are being irrigated, the collection device collects a sample of the FS 115 being applied. In the case of sprinkler irrigation, a collection device such as, e.g., an open container may be positioned in the vicinity of the group of suction probes 106 to collect an FS sample from the discharge of the sprinkler. These examples provide a sample of the FS 115 that is representative of that provided over the entire irrigation time period.

The FS samples may then be provided for analysis. Analysis of the FS 115 provides information regarding the fertilizer contributions and the conditions of assimilation (e.g., pH, electrical conductivity, and ionic relationship). When considered with the aqueous solution analysis and the soil sample analysis, it is possible to evaluate the interaction of the FS 115 with the plant 109 and soil 103 (FIG. 1). For example, plant absorption and/or utilization of nutrients as well as soil interactions such as precipitation, solubility, ion desorption, etc. may be evaluated.

Samples of irrigation water and tissue of the plants 109 may also be obtained and provided for analysis. Sampling protocols may be followed to ensure that the samples represent a true indication of the irrigation water composition. Irrigation water samples may be obtained at the source, before filtering, after filtering, and/or before addition of one or more additives such as, e.g., nutrients and/or chemicals to form the FS 115. Composition of the irrigation water may be used as, e.g., a baseline in determining adjustments to the additive(s) for the FS 115. For example, mineral salt content may be adjusted based on the analysis of the irrigation water to meet the nutritional needs of the plants 109. Sampling protocols may also be followed to ensure that the samples represent a true indication of the plant tissue composition. Plant tissue samples may be leaves that are neither old nor too young such as, e.g., the first 5-6 leaves after the apex of a shoot of the plant 109. Other tissue samples include sap, stems, roots, flowers fruit, seeds, etc. that may be obtained during the growth of the plant 109. Sampling protocols may be different for various plant materials such as, e.g., leaf cultivation, sap, fruit, and flowers. Sampling protocols will depend upon the species of the plant 109. Analysis of the tissue samples can provide information of the nutritional status of the plant 109 indicating absorption and/or utilization of the additives supplied in the FS 115. Analysis may take into account evolutionary interpretations considering seasonal changes of the type of plant materials and variety level and static interpretations without consideration of seasonal changes.

The analysis of the soil samples, aqueous samples, irrigation water samples, and/or plant tissue samples provides information that may be used in the evaluation of the availability, balances, intakes, and rate of use of the nutrients over the growth cycle of the plant 109. For example, analysis of the soil sample at each depth can provide information about the availability of leaching nutrients, allowing evaluation of the ion dynamics within the soil 103 (FIG. 1). In addition, it allows for evaluation of the rate of lixiviation of the fertilizers in the root activity zone 112 (FIG. 1) and/or the behavior of different additives when added to the soil 103. The information may be used, at least in part, to determine adjustments and/or changes to the FS 115 (FIG. 1) that is applied to the soil 103 with the root activity zone 112.

The acquisition and analysis of aqueous samples may also be used for static leaching processes. For example, the process may be applied in "Heap" and "Dump" leaching for, e.g., copper lixiviation, oxidized and primary minerals as porphidic or massive sulphides, with the participation of microorganisms in the catalysis of chemical reactions. In addition, monitoring and control of the soil condition may be applied to uranium leaching, gold leaching from oxidized materials or in free form, and/or bio-leaching of gold in sulphides minerals.

In general, static leaching processes are based on bed packed percolation techniques, which are prepared for that purpose and may be distinguished as two main groups: "heap leaching" and "dumping leaching." The difference between the two groups is based on the volume, control of the process, and the concentrations of the substances to be extracted in the solid matter. "Heap leaching" requires less time to lixiviate, lower volumes of materials, greater legal requirements, and greater operational control. In both cases, the process is based on gaining accurate and reliable information about what happens inside the piles during the heap and dump leaching. Three chemical phases interact in the chemical processes: solid material, the leaching agent, and gas that is dissolved in the liquid or introduced in a forced manner. Moreover, in many cases leaching procedures count on the participation of microorganisms. These proceedings add additional information to the historical analysis of percolation, which allows operational measures to be taken to correct and improve the functioning of the process.

Initially, a number of suction probes 106 are installed within the pile as described above. The number of probes 106 may be based upon the volume and surface being examined. The suction probes 106 may be situated at various depths to obtain the widest range of information possible. For heap leaching, probe placement can be carried out during construction. Dump leaching may also have one or more suction probe(s) 106 installed during construction but, due to the longevity and long term exploitation, suction probes 106 may be installed after the dump has been built. This may be accomplished by forming (e.g., drilling) a small perforation to introduce a suction probe 106. After installation, aqueous samples may be obtained using the suction probes 106 as described above. The sampling schedule (and durations) may be based upon the monitored process. The collected aqueous samples may be analyzed to determine data such as, e.g., temperature, oxygen and other dissolved gases, pH, electro conductivity, metal concentrations, other dissolved cations and anions, concentration and/or types of microorganisms, and/or organic substances produced as a result of bacterial digestions. Based on the analysis data, recommendations may be offered in terms of, e.g., volumes of flow, concentration of lixiviating agents, and/or air or gas flow to be injected.

The "in situ" on site monitoring may also be applied in solid-liquid extraction processes used in the cleaning and decontamination of contaminated lands. Applications can include metal contaminated soil close to urban areas or other large facilities which make extraction and transport of the contaminated soil too complicated. Examples include, but are not limited to, metallurgic facilities (smelting, steel industry, transformers, etc.), zones with high concentrations of minerals and metals, and/or stations or facilities where materials are transferred, loaded or unloaded. In cases where the treatment is made in soil that has not been moved to an external waste management platform, suction probes 106 may be used to permit operational performance follow-ups. The suction probes 106 allow for a simple implementation that can be used for environmentally friendly monitoring. Suction probes 106 may be placed and aqueous samples obtained as described above. The information gained from the analysis of the aqueous samples may be used to prove the efficiency of the applied processes and to determine any further adjustments or corrections to conclude the decontamination task.

Following decontamination of soil or other degraded spaces, medium or long term monitoring may be established using installed suction probes 106. Suction probes can be placed for effective monitoring. In general, for homogenous grounds suction probes 106 are placed a various depths for sampling throughout the soil substrate. In non-homogenous grounds, probes 106 may be positioned to account for the soil variations. Aqueous samples can be obtained from the probes 106 to monitor and identify possible metabolites from substances that are not recovered completely. Samples may be analyzed to determine the behavior of substances within the soil and how they degrade and/or mobilize under different climatic conditions. Once the behavior is known, scheduling of measurements can be optimized and the number of and time between each sampling may be spaced out. When fully optimized, it may be that suction probes 106 will not provide liquid phase samples, which may indicate good functioning of the monitored system and a lack of a liquid phase in the activity zone. Whenever the situation changes, a gathered sample may be analyzed and the parameters associated with the origin of the contamination. Corrective actions may be proposed based at least in part upon the analysis results, followed by additional monitoring and testing.

Suction probes 106 may also be installed and used to provide alerts and/or prevent leaks and spoilages in processes where barriers are used to protect surrounding environments. In situations where there is a risk of spoilage or possible transfer of products or residues to the ground, early detection of seepage into the surrounding soil can allow for a rapid response.

For example, monitoring may be applied in industrial facilities with risk of leakage or losses such as, e.g., "heap" and/or "dump" leaching of different metals (e.g., copper, uranium, gold, nickel, or others), dumping sites for hazardous wastes, urban garbage dumps or sites, and/or chemical industrial areas with pools or ponds. The use of artificial protection barriers and/or highly impermeable layers in combination with monitoring with suction probes 106 reduces the chance of economic loss or negative environmental impact. The configuration and extent of the barrier used can be taken into consideration to determine the placement of suction probes 106. The suction probes 106 may be vertically situated outside the barrier at one or more depths and/or one or more angles of inclination. A sampling schedule may be defined detailing the frequency and analysis of aqueous samples obtained from the suction probes 106. Immediate notification may be provided to an operator upon detection of an aqueous sample. A protocol may define the type of reporting when there is an aqueous sample as well as when no aqueous solution is present for sampling. Analysis of the aqueous sample can be used to determine if the leak is a similar composition to the substances used by the facility. In some cases, corrective measures may be recommended based at least in part upon the analysis results.

Figure 3:
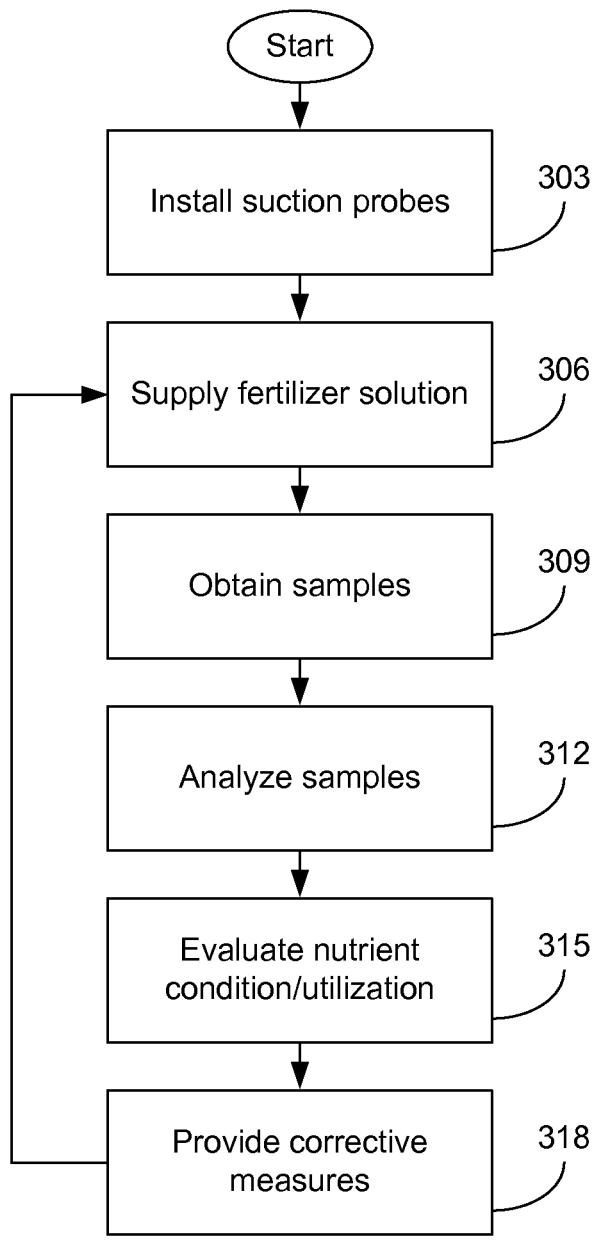
FIG. 3 is a flow chart illustrating an example of monitoring and control of the soil condition according to various embodiments of the present disclosure.

Referring to FIG. 3, shown is a flow chart illustrating an example of monitoring and control of the soil condition according to various embodiments of the present disclosure. Beginning with block 303, one or more suction probes 106 (FIG. 1) may be installed at one or more depths in the soil substrate 103 (FIG. 1). The soil substrate 103 may include a root activity zone 112 (FIG. 1) of a plant species in the soil substrate 103. One or more of the suction probe(s) 106 may be within the root activity zone 112. The suction probes 106 include porous capsules 203 (FIG. 2) that allow for hydraulic conduction of aqueous solutions from the soil substrate 103 and/or root activity zone 112 when a vacuum is drawn. Holes may be drilled into the soil substrate 103 and one or more suction probe(s) 106 inserted at one or more depths. Samples of the soil substrate 103 may also be obtained at a variety of depths at this time and analyzed to determine the composition of the soil substrate 103. In block 306, a fertilizer solution 115 (FIG. 1) may be supplied to the plants 109 (FIG. 1) by irrigating with, e.g., a drip line or a sprinkler. A sample of the FS 115 may also be collected over a portion of the entire irrigation period in block 306.

Samples are obtained in block 309. For instance, a sample (or samples) of aqueous solution(s) may be obtained from the suction probe(s) 106 (FIG. 1). A vacuum is drawn on each suction probe 106 to induce hydraulic conduction of aqueous solutions from the soil substrate 103 and/or root activity zone 112 (FIG. 1). After a predefined time period (e.g., 48 hours), one or more sample(s) of the aqueous solution is extracted from the suction probe(s) 106 and provided for analysis in block 312. The aqueous samples may be analyzed for pH; electrical conductivity; anions such as, e.g., $NO_3^-$, $H_2PO_4^-$, $HCO_3^-$, $CO_3^=$, $SO_4^=$, and/or $Cl^-$; cations such as, e.g., $Ca^{++}$, $Mg^{++}$, $K^+$, $Na^+$, and/or $NH_4^+$; and microelements such as, e.g., B, Fe, Mn, Cu, Zn, Mo, and/or Urea. A sample of the FS 115 collected over the irrigation period may also be obtained from a collection device in block 309 and the composition analyzed in block 312. Plant tissue samples and/or an irrigation water sample may also be obtained in block 309 and analyzed in block 312. The FS sample, as well as an irrigation water sample, may be analyzed for the same elements as the aqueous solutions. The tissue sample may be analyzed for, e.g., nitrogen, phosphorous, sulfur, chlorine, calcium, magnesium, sodium, potassium, boron, iron, manganese, copper, zinc, and/or molybdenum.

In block 315, the chemical composition and/or the nutrient utilization are evaluated based at least in part upon the sample analysis of block 312. Chemical, mineral, and/or nutrient levels in the root activity zone 112 (FIG. 1) may be examined and compared to predefined levels associated with the plant species. In some implementations, the levels used for comparison may vary with the phenological stage of the plant 109. Concentrations of marker ions (which are present in the root activity zone 112 but are generally not absorbed by the plant 109) such as, e.g., chlorides and/or sodium at the different depths may also be examined and used to evaluate, e.g., crop absorption of water and evaporation effect. In addition, ion concentrations with respect to one or more marker ions may be used to evaluate the utilization of various nutrients. For example, chlorides may be used to determine utilization of nitrogen and/or other anions such as, e.g., $NO_3^-$, $H_2PO_4^-$, and $SO_4^=$, sodium may be used to determine utilization of potassium, calcium, magnesium and/or other cations such as, e.g., $NH_4^+$, and the combination of chlorides and sodium (e.g., the average of both) may be used to determine utilization of phosphorous or other chemicals and/or nutrients. Based at least in part upon the utilization, consumption of the ions, chemicals, and/or nutrients may also be determined. Effects of the soil composition may also be taken into account during the evaluations. Also, plant tissue analysis may also be used to evaluate the absorption and/or utilization of nutrients by the plants. The evaluation may also take into account variations in the analyzed sample obtained over the growth of the plants as well as those obtained at different locations within the field. In some cases, analysis information may be compared with broader agricultural segment information during the evaluation.

Corrective (or remedial) measures are provided in block 318 based at least in part upon the evaluation of block 315. For example, corrective measures may include increasing the water dosage to dilute the ions in the root activity zone 112 and/or the soil substrate 103. In some implementations, corrective measures may include irrigation of the plants 109 using irrigation water without the addition of other additives such as, e.g., fertilizers or chemicals. In other cases, the amount of additive(s) to be included in the FS 115 or adjustments to proportions between the chemical components in the FS 115 may be provided. In some implementations, the corrective measures may be automatically applied to the next application of FS 115. In some implementations, other factors may also be considered when determining corrective measures. For example, weather conditions (e.g., temperature, rainfall, wind, etc.) and applied fertilization strategies (e.g., UF, fractionation, anticipate DFR, etc.) may be accounted for.

The flow chart repeats the monitoring and control of the soil condition by returning to block 306 where another FS 115, which is based upon the adjustments provided in block 318, is again supplied to the plants 109. In this way, the condition of the soil may be monitored and controlled in a cyclic or continuous manner to improve crop growth and production.

Figure 4:
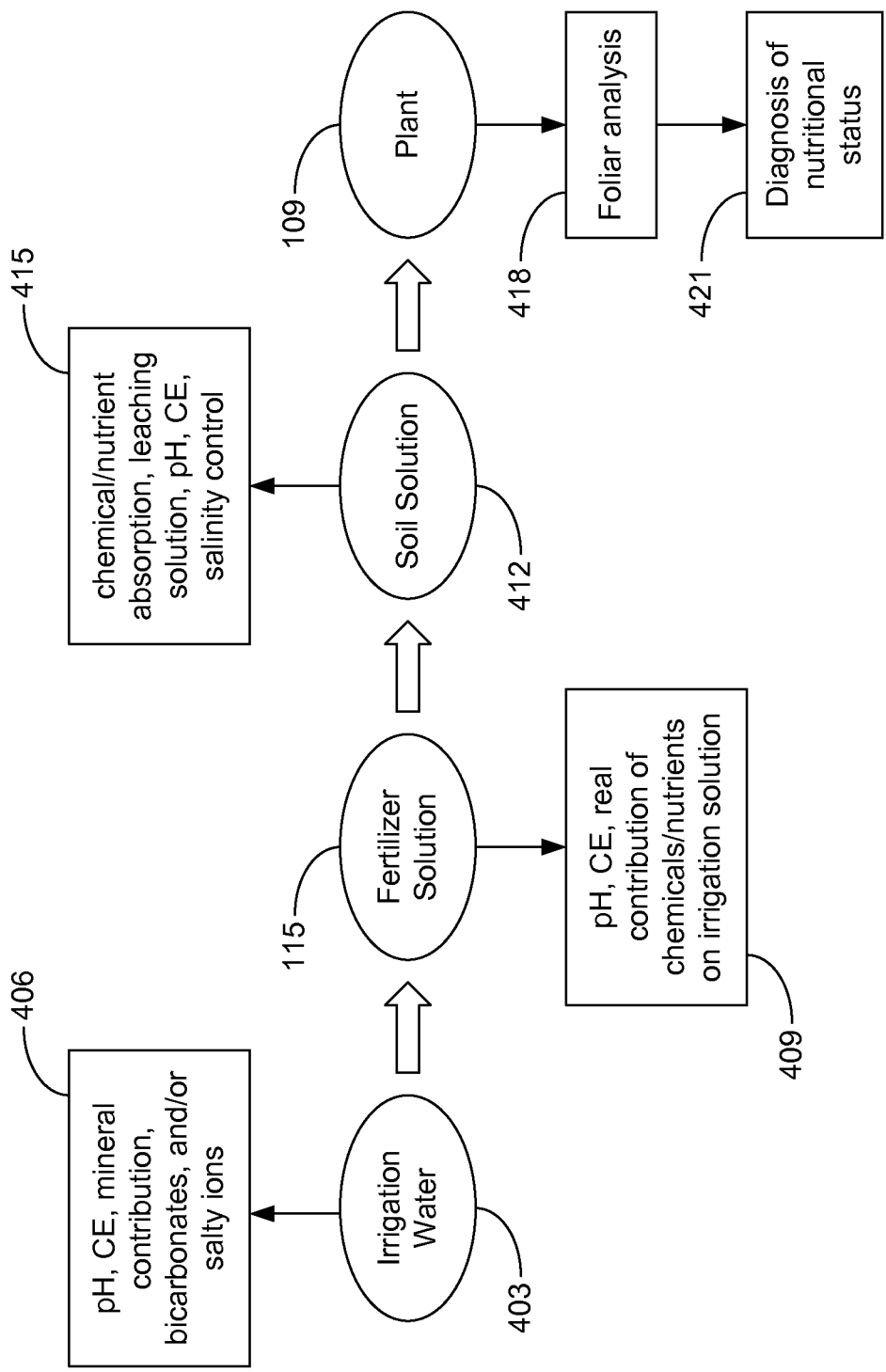
FIG. 4 is a flow chart illustrating an example of sample analysis according to various embodiments of the present disclosure.

FIG. 4 illustrates examples of the composition evaluation that may be carried out on various obtained samples in block 315 (FIG. 3). For example, analysis of a sample of the irrigation water 403 may provide information 406 including, e.g., pH level, electrical conductivity (CE), mineral contributions, bicarbonates, salty ions, etc. In addition, analysis of the FS 115 may provide information 409 about the irrigation water 406 may include, e.g., pH level, electrical conductivity (CE), the contribution of additives such as, e.g., chemicals and/or nutrients on the irrigation solution, etc. Soil solutions 412 (e.g., aqueous solutions and/or soil samples) may also be analyzed to determine soil composition information 415 such as, e.g., chemical and/or nutrient absorption, leaching, pH level, electrical conductivity (CE), salinity levels, etc. Samples of the plant 109 may also be obtained for foliar analysis 418 which may be used to diagnose the nutritional status 421 of the plant 109.

Each condition of the obtained samples may be analyzed and evaluated individually or in conjunction with conditions of the same or other samples in block 315 (FIG. 3) to determine the corrective measures of block 318 (FIG. 3). For example, pH level may be evaluated throughout the root activity zone 112 of the plants 109 to quantify the acidity of the soil substrate 103 (FIG. 1) and determine corrective solutions if needed. In general, pH levels are maintained in a range of about 6-8, about 6.5-8, or about 6.5-7.5 by adjusting the composition of the supplied FS 115 (FIG. 1). Lower pH levels can pose a risk by increasing the solubility of metals such as, e.g., Al, Mn, Fe, Cu, and Zn. A pH<5 could produce Al and Mn concentrations that may be toxic. Higher pH levels reduce the solubility of metals, but may need to use chelating agents for Mn, Fe, and Zn. For example, EDTA may be used for a pH<6.7, DTPA may be used for a pH between 6.7 and 7.8, and EDDHA may be used for a pH>7.8. Conditions based upon the analysis of the soil samples may also be considered when evaluating the effect of the FS 115 on pH levels.

The salinity condition throughout the root activity zone 112 may also be evaluated based upon, e.g., electrical conductivity (EC) and chloride and sodium content within the aqueous samples to provide an indication of salts and/or fertilizer accumulation and salt leaching in the root activity zone 112. Criteria to evaluate the EC throughout the root activity zone 112 will depend on the plant species. An example of general criteria that may be used to evaluate the chloride and Na concentration ratios is provided in TABLE 1 below. The chloride concentration ratio ($CR_{Cl}$) is the ratio of the average Cl level in the aqueous samples from throughout the root activity zone 112 to the Cl level in the supplied FS 115 and the sodium concentration ratio ($CR_{Na}$) is the ratio of the average Na level in the aqueous samples from throughout the root activity zone 112 to the Na level in the supplied FS 115.

TABLE 1

| Cl level | Cl concentration ratio | | |
|---|---|---|---|
| (meq/l) | Low | Medium | High |
| <3 | <1.5 | 1.5-2 | ≥2 |
| ≥3 | <1.2 | 1.2-1.5 | ≥1.5 |

TABLE 1-continued

| Na level | Na concentration ratio | | |
|---|---|---|---|
| (meq/l) | Low | Medium | High |
| <3 | <1.5 | 1.5-2 | ≥2 |
| ≥3 | <1.2 | 1.2-1.5 | ≥1.5 |

The concentration ratio may also be applied to other ions, chemicals, and/or nutrients within the root activity zone 112 and the FS 115. For example, the concentration ratio for an ion, chemical, or nutrient X in an aqueous sample may be expressed as:

$$CR_X = X_{AS}/X_{FS}$$

where $X_{AS}$ is the average level of the ion, chemical, or nutrient X in the aqueous samples from the various depths of the root activity zone 112 and $X_{FS}$ is the level of the ion, chemical, or nutrient X in the supplied FS 115.

The EC concentration ratio ($CR_{EC}$) may also be used to evaluate salinity conditions within the root activity zone 112. The $CR_{EC}$ is the ratio of the average EC level in the aqueous samples from throughout the root activity zone 112 to the EC of the supplied FS 115. When the $CR_{EC}$ is about 1-1.2, this can indicate that the soil 103 is very permeable. In this case, $CR_{Cl}$ and $CR_{Na}$ being about 1-1.2 can indicate low plant activity and/or high drainage. When $CR_{Cl}$ and $CR_{Na}$ are >1.5, this can indicate high plant activity and/or limited drainage. If the EC decreases progressively with depth, this may indicate a strong response from the plant root system (absorption) that is reducing salts from the root activity zone 112. In the case where the $CR_{EC}$ indicates low permeability (>1.5), salts are entering the root activity zone 112 faster than they are removed by the plant roots or drained from the root activity zone 112. High root absorption may be indicted by high rates of fertilizer use while low plant activity may be indicated by low rates of fertilizer use.

Crop development and productivity can be limited by the high saline levels indicated by high EC. If high levels of $Cl^-$ and $Na^+$ are present, there is a risk of phytotoxicity, antagonism, osmotic stress, and soil peptization. Washing irrigations and maintaining the soil moisture at field capacity can reduce the concentrations, however $Cl^-/NO_3^-$ and $Na^+/(K^+ + Ca^{++} + Mg^{++})$ ratios should to be accounted for by maintaining the ratios at 1 (maximum). If high levels of $SO_4^{2-}$, $Ca^{++}$, and $Mg^{++}$ are present, then the irrigation is basically osmotic and washing irrigations and maintaining the soil moisture at field capacity is needed. High $Ca^{++}$ and $Mg^{++}$ levels can antagonize $K^+$ absorption and $H_2PO_4^-$ precipitation, so an increase in these nutrient supplies is desirable. Where a mix of both conditions is present, a mix of corrective measures may be used. Acceptable salinity levels and/or limits can vary based upon the plant species and corrective measures may be determined accordingly.

Macronutrients such as, e.g., phosphorous, nitrogen, potassium, calcium, and magnesium may also be analyzed and evaluated for availability and to identify nutrient imbalances and risks of fertilizer leaching. Concentration ratios (CR) may be determined based upon one or more ion levels in the aqueous samples and FS 115. A utilization rate (UR) of the nutrients with respect to a marker ion may also be determined based at least in part upon the corresponding CRs. For an ion, chemical, or nutrient X, the utilization rate may be expressed as:

$$UR_X = (1 - (X_{AS}/(X_{FS} \times CR_{MKR}))) \times 100$$

where $X_{AS}$ is the average level of the ion, chemical, or nutrient X in the aqueous samples from the various depths of the root activity zone 112, $X_{FS}$ is the level of the ion, chemical, or nutrient X in the supplied FS 115, and $CR_{MKR}$ is the concentration ratio of the marker ion(s) such as, e.g., chlorides and/or sodium. A consumption index (CI) of the nutrients may also be determined based at least in part upon the corresponding URs. For an ion, chemical, or nutrient X, the consumption index may be expressed as:

$$CI_X=(UR_X/100)\times X_{FS}.$$

The $UR_X$ and $CI_X$ of the ion, chemical, or nutrient X may be used as key indicators in the evaluation. For example, the $UR_X$ and $CI_X$ may be compared with predefined levels or ranges to determine if corrections may be recommended.

For phosphorous, the condition of $H_2PO_4^-$ may be examined. In the aqueous samples from the root activity zone 112, $H_2PO_4^-<10$ ppm can indicate low availability, $H_2PO_4^-$ in the range of 10-20 ppm can indicate medium availability, and $H_2PO_4^->20$ ppm can indicate high availability. In the FS 115, $H_2PO_4^-<20$ ppm can provide a low contribution, $H_2PO_4^-$ in the range of 20-40 ppm can provide a medium contribution, and $H_2PO_4^->40$ ppm can provide a high contribution. The $H_2PO_4^-$ level in the FS 115 should not be higher than 10% of the $NO_3^-$ level. The utilization rate and consumption index for phosphorous may be determined based upon the levels of $H_2PO_4^-$. Broadcast fertilization may be periodically applied with $H_2PO_4^-<6$ ppm.

For nitrogen, the condition of $NO_3^-$, $NH_4^+$ and Urea may be analyzed and evaluated. In the aqueous samples from the root activity zone 112, $NO_3^-<2$ meq/l can indicate low availability, $NO_3^-$ in the range of 2-4 meq/l can indicate medium availability, and $NO_3^->4$ meq/l can indicate high availability. A high $NO_3^-$ level at the bottom of the root activity zone 112 may indicate a risk of leaching. The nitrogen utilization rate ($UR_N$) may also be considered where:

$$UR_N=(1-(N_{AS}/(N_{FS}\times CR_{Cl})))\times 100$$

where $N_{AS}$ is the average level of N within the root activity zone 112, which may be estimated as the average of $NO_3^-+NH_4^++$Urea in the aqueous samples at each depth, $N_{FS}$ is the level of N in the FS 115 estimated by the average of $NO_3^-+NH_4^++$Urea, and $CR_{Cl}$ is the concentration ratio of the chloride marker ion. A $UR_N<33\%$ can indicate a low use (e.g., excessive contribution or low activity during the period), $UR_N$ in the range of 33-66% ppm can indicate a medium use (e.g., adequate contribution), and $UR_N>66\%$ can indicate a high contribution (e.g., a high activity period or insufficient contribution). The nitrogen consumption index may also be determined where:

$$CI_N=(UR_N/100)\times N_{FS}.$$

The $CI_N$ may also be evaluated based upon predefined levels or ranges.

An example of general criteria that may be used to evaluate the nitrogen and chloride ratio is provided in TABLE 2 below. Indications of $NH_4^+$ concentrations >0.3 meq/l may be an indication of an incipient reducing environment that can lead to root suffocation problems. Reducing environments may be corrected by, e.g., reduction of FS doses, pulse irrigation, or application of strong oxidizing chemicals such as, e.g., potassium permanganate and/or others.

TABLE 2

|  | Cl level | N/Cl⁻ ratio | |
|---|---|---|---|
|  | meq/l | Low | Adequate |
| Fertilizer Solution | <5 | <1 | ≥1 |
|  | >5 | <1 | ≥1 |
| Aqueous Solution | <5 | <0.75 | ≥0.75 |
|  | >5 | <0.5 | ≥0.5 |

For potassium, the condition of $K^+$ may be analyzed and evaluated. In the aqueous samples from the root activity zone 112, a level of $K^+<0.3$ meq/l can indicate low availability, $K^+$ in the range of 0.3-0.6 meq/l can indicate medium availability, and $K^+>0.6$ meq/l can indicate high availability. In the FS 115, $K^+<0.75$ meq/l can provide a low contribution, $K^+$ in the range of 0.75-1.5 meq/l can provide a medium contribution, and $K^+>1.5$ meq/l can provide a high contribution. The potassium utilization rate ($UR_K$) may also be considered where:

$$UR_K=(1-(K_{AS}/(K_{FS}\times CR_{Cl})))\times 100$$

where $K_{AS}$ is the average level of $K^+$ in the aqueous samples at each depth in the root activity zone 112, $K_{FS}$ is the level of $K^+$ in the FS 115, and $CR_{Cl}$ is the concentration ratio of the chloride marker ion. A $UR_K<33\%$ can indicate a low use (e.g., excessive contribution or low activity during the period), $UR_K$ in the range of 33-66% ppm can indicate a medium use (e.g., adequate contribution), and $UR_K>66\%$ can indicate a high contribution (e.g., high activity period or insufficient contribution). The potassium consumption index may also be determined where:

$$CI_K=(UR_K/100)\times K_{FS}.$$

The $CI_K$ may also be evaluated based upon predefined levels or ranges.

In addition, the ratio of $K^+$ with respect to other cations (or anions), which may affect utilization of $K^+$ by the plant 109, may be examined. For example, the ratio of $K^+/(Na^++Ca^{++}+Mg^{++})$ may also be evaluated. An example of general criteria that may be used to evaluate the level of $Na^++Ca^{++}+Mg^{++}$ and the $K^+$ ratio is provided in TABLE 3 below.

TABLE 3

|  | $Na^+ + Ca^{++} + Mg^{++}$ level | $K^+/(Na^+ + Ca^{++} + Mg^{++})$ level | |
|---|---|---|---|
|  | meq/l | Low | Adequate |
| Fertilizer Solution | <7 | <0.2 | ≥0.2 |
|  | >7 | <0.15 | ≥0.15 |
| Aqueous Solution | <10 | <0.15 | ≥0.15 |
|  | >10 | <0.1 | ≥0.1 |

For calcium, the condition of $Ca^{++}$ may be analyzed and evaluated. In the aqueous samples from the root activity zone 112, $Ca^{++}<3$ meq/l can indicate low availability, $Ca^{++}$ in the range of 3-4 meq/l can indicate medium availability, and $Ca^{++}>4$ meq/l can indicate high availability. The calcium utilization rate:

$$UR_{Ca}=(1-(Ca_{AS}/(Ca_{FS}\times CR_{Na})))\times 100$$

and/or calcium consumption index:

$$CI_{Ca}=(UR_{Ca}/100)\times Ca_{FS}.$$

may also be considered, where $Ca_{AS}$ is the average level of $Ca^{++}$ in the aqueous samples at each depth in the root activity zone 112, $Ca_{FS}$ is the level of $Ca^{++}$ in the FS 115, and $CR_{Na}$ is the concentration ratio of the sodium marker ion. The $UR_{ca}$ and/or $CI_{ca}$ may be evaluated based upon predefined levels or ranges.

In addition, the ratio of $Ca^{++}$ with respect to other cations (or anions), which may affect utilization of $Ca^{++}$ by the plant 109, may be examined. For example, the ratios of $Ca^{++}/Na^+$ and $Ca^{++}/Mg^{++}$ may also be evaluated. Examples of general criteria that may be used to evaluate the ratios are provided in TABLES 4 and 5 below.

TABLE 4

| | $Na^+$ level | $Ca^{++}/Na^+$ ratio | |
|---|---|---|---|
| | meq/l | Low | Adequate |
| Fertilizer Solution | <3 | <1 | ≥1 |
| | >3 | <0.75 | ≥0.75 |
| Aqueous Solution | <4 | <1 | ≥1 |
| | >4 | <0.75 | ≥0.75 |

For magnesium, the condition of $Mg^{++}$ may be analyzed and evaluated. In the aqueous samples from the root activity zone 112, $Mg^{++}<1.5$ meq/l can indicate low availability, $Mg^{++}$ in the range of 1.5-2 meq/l can indicate medium availability, and $Mg^{++}>2$ meq/l can indicate high availability. The magnesium utilization rate:

$$UR_{Mg}=(1-(Mg_{AS}/(Mg_{FS} \times CR_{Na}))) \times 100$$

and/or magnesium consumption index:

$$CI_{Mg}=(UR_{Mg}/100) \times Mg_{FS}.$$

may also be considered, where $Mg_{AS}$ is the average level of $Mg^{++}$ in the aqueous samples at each depth in the root activity zone 112, $Mg_{FS}$ is the level of $Mg^{++}$ in the FS 115, and $CR_{Na}$ is the concentration ratio of the sodium marker ion. The $UR_{Mg}$ and/or $CI_{Mg}$ may be evaluated based upon predefined levels or ranges.

In addition, the ratio of $Mg^{++}$ with respect to other cations (or anions), which may affect utilization of $Mg^{++}$ by the plant 109, may be examined. For example, the ratio of $Ca^{++}/Mg^{++}$ may also be evaluated. An example of general criteria that may be used to evaluate the ratio is provided in TABLE 5 below.

TABLE 5

| | $Ca^{++}$ level | $Ca^{++}/Mg^{++}$ ratio | |
|---|---|---|---|
| | meq/l | Low | Adequate |
| Fertilizer Solution | <5 | <3 | ≥3 |
| | >5 | <2 | ≥2 |
| Aqueous Solution | <6 | <3 | ≥3 |
| | >6 | <2 | ≥3 |

Microelements (or micronutrients) such as, e.g., iron, manganese, zinc, copper, boron, etc. may also be analyzed and evaluated for availability and to identify toxicity risks and nutrient imbalances. An example of general criteria that may be used to evaluate microelements in the root activity zone 112 and FS 115 is provided in TABLE 6 below.

TABLE 6

| | Fe (ppm) | Mn (ppm) | Zn (ppm) | Cu (ppm) | B (ppm) |
|---|---|---|---|---|---|
| Low | <0.7 | <0.5 | <0.5 | <0.25 | <0.15 |
| Medium | 0.7-3 | 0.5-2 | 0.5-2 | 0.25-1 | 0.15-0.6 |
| High | >3 | >2 | >2 | >1 | >0.6 |

The effect(s) of nutrients in the FS 115 on the plant 109 is also considered when determining a corrective measure such as adjusting nutrient levels in the FS 115 for the next application. FIG. 5 illustrates the relationship between added nutrients and their effect in the plant 109. The absorption synergies of the nutrients may also be taken into account when determining the corrective measure of block 318 (FIG. 3). An example of the synergies between the nutrients is provided in TABLE 7 below.

TABLE 7

| Assimilation of: | Reduces the assimilation of: | Increases the assimilation of: |
|---|---|---|
| $NH_4^+$ | Mg, Ca, K, Mo | Mn, P, S, Cl |
| $NO_3^-$ | Fe, Zn | Ca, Mg, K, Mo |
| P | Cu, Zn | Mo |
| K | Ca, Mg | Mn (acidic soils) |
| Ca | K | Mn (basic soils) |
| Mg | Cu, Zn | Mo |
| Fe | Cu, | |
| Zn | Mo | |
| Cu | Zn, Ca, Mo | |
| Mn | | |

Evaluation of the conditions for determination of the appropriate corrective measures may vary based upon plant species. For example, fruits and vegetables may flourish under very different nutrient conditions. In addition, the tolerance of the plant 109 to various ion, chemical and/or nutrient concentrations may also affect the proposed corrective measures. Appendix A includes examples of evaluation guidelines for peach and nectarine plant species. Appendix A includes guidelines for evaluation of irrigation water quality, foliar (plant tissue), FS and aqueous soil samples. In addition, Appendix A outlines allocation of irrigation according to the growth cycle for both young and adult plants and includes diagnosis and observed corrections based upon aqueous sample evaluation. Correction factors are determined based upon various evaluated conditions to determine the irrigation allocation. The amount of one or more additive(s) may be further refined based upon the chemical composition of the aqueous samples and the irrigation water.

Monitoring and control of the soil conditions may be implemented as an application executable by a computing device. For example, evaluation of the analyzed samples (block 315 of FIG. 3), as well as determination and provision of corrective measures (block 318 of FIG. 3), may be implemented with a soil monitoring and control application. Corrective measures may be determined based at least in part upon evaluation of the analyzed samples using pattern recognition, neural network evaluation, and/or other rule based identification methods as can be appreciated. In addition, supplying a fertilizer solution (FS) (block 306 of FIG. 3), obtaining samples (block 309 of FIG. 3), and/or analyzing the samples (block 312 of FIG. 3) may be automated and controlled by the soil monitoring and control application. The soil monitoring and control application may also allow access to stored analysis data through generated network pages or other graphical displays.

Appendix B includes examples of graphical displays that may be rendered for use by a user of the soil monitoring and control application. The graphical displays may allow the user to access the chemical and/or nutritional monitoring of monitored crops by accessing, e.g., user profiles, evolutionary dynamics, phytomonitoring, comparison of plot information, and benchmarking. Evolutionary dynamics allow the user to monitor changes or patterns in various chemical and/or nutrient concentrations in the aqueous samples (soil solution), plants, fruit, or other contributing factors such as, e.g., irrigation and fertilization. Upper and lower limits may be included as guidelines in the graphical representations. These limits may vary over the life cycle of the plant species. Comparison of plots (or monitored areas) allows corrective measures to be tailored for each monitored area. Phytomonitoring allows the user to compare the effects of multiple parameters to other monitored environmental conditions. As indicated in Appendix A, the allocation of irrigation can vary with the crop cycle of the plant species as well as with the age of the plant.

Evaluation results for various parameters for irrigation water, soil composition, and plants may also be presented for user access. The evaluation results may also include corrective measures as discussed above, which are identified based upon the evaluation results. For example, the soil monitoring and control application may provide one or more additives for addition to the irrigation water to improve the chemical composition of the root activity zone to increase growth and productivity. A user may also access client databases to evaluate historical data. One or more monitored parameter(s) may be selected for rendering. The historical information may be displayed as a spread sheet or may be rendered in one of a plurality of graphical formats.

In addition, a variety of reports may be generated by the soil monitoring and control application. For example, automatic interpretations of the sample analysis may be provided in a report such as, e.g., nutritional analysis of the root activity zone as shown in Appendix C. Such a report can include profile information related to, e.g., salinity, pH, nutritional/chemical composition, and micro and/or macro elements. The report may also include corrective actions that may be implemented to restore and/or maintain the chemical composition of the soil substrate in balance. For example, the report may indicate suitable washes and/or additive(s) for application to the soil substrate. The report may also include the amount of additive(s) that should be added to irrigation water, based at least in part upon the results of the aqueous solution analysis, to restore a desirable chemical/nutritional composition to the root activity zone and/or soil substrate. The amount of additive(s) may be based upon the evaluated levels of ions, chemicals, and/or nutrients. For example, a table or database may provide a recommended amount based at least in part upon the concentration levels, concentration ratio (CR), utilization rate (UR), and/or consumption index (CI). In other implementations, the recommended amount may be determined based at least in part upon the evaluations of the concentration levels, CR, UR, and/or CI using pattern recognition, neural network evaluation, and/or other rule based identification methods as can be appreciated.

Figure 6:
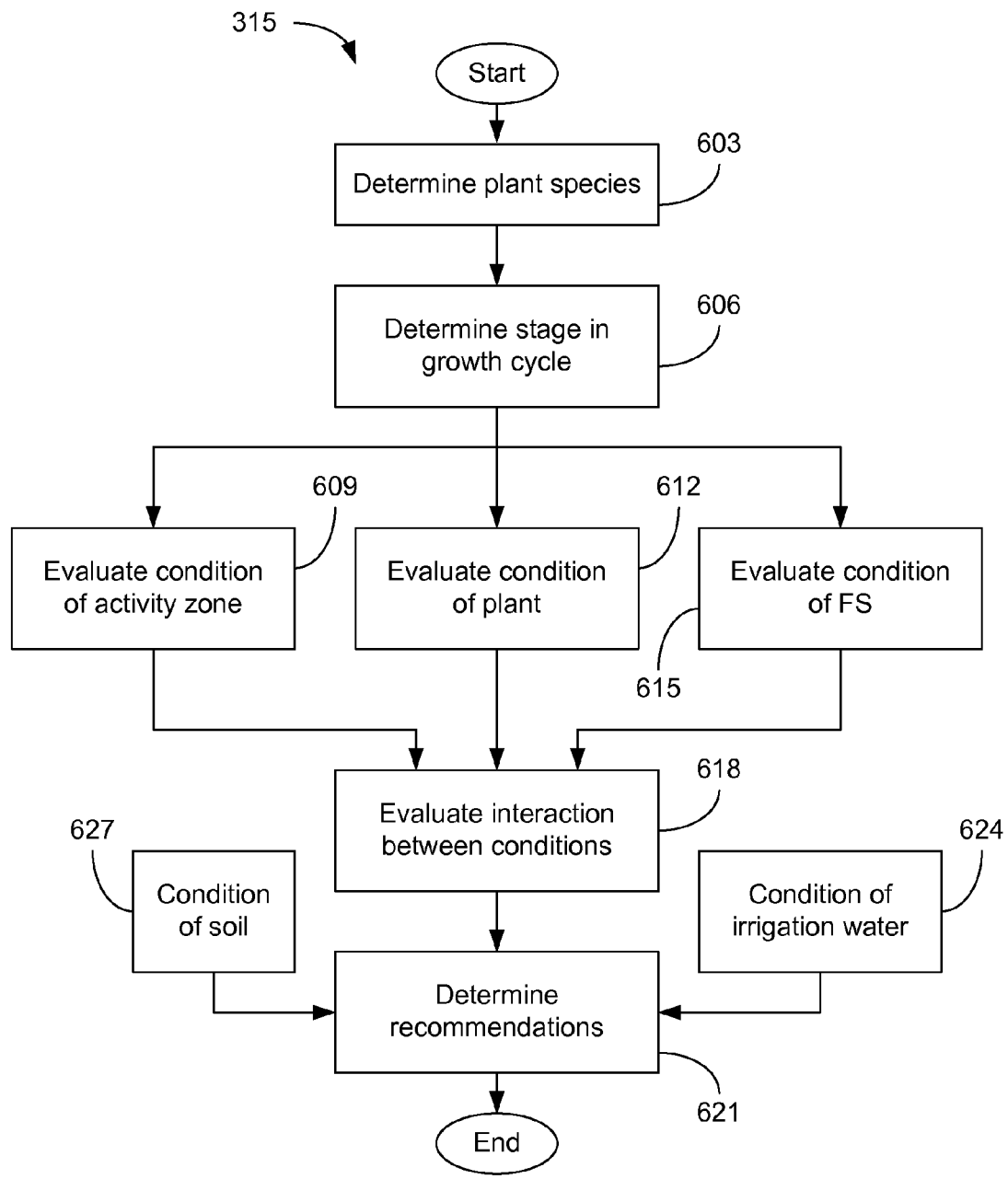
FIG. 6 is a flow chart illustrating an example of the composition and/or utilization evaluation of FIG. 3 according to various embodiments of the present disclosure.

Referring next to FIG. 6, shown is a flow chart illustrating an example of the evaluation that may be carried out in block 315 of FIG. 3. Chemical composition, concentration ratio (CR), utilization rate (UR), and/or consumption index (CI) can be evaluated based at least in part upon the sample analysis of block 312 (FIG. 3). Each condition of the obtained samples may be analyzed and evaluated individually or in conjunction with conditions of the same or other samples to determine the corrective measures of block 318 (FIG. 3).

Beginning with block 603, a plant species is determined for the evaluation of the analyzed samples. For example, a user may identify the species of the plant 109 (FIG. 1) through a user interface or the species may be determined based upon information associated with the obtained samples or the location the samples were obtained from (e.g., from a user profile stored in a data store). The stage in the growth cycle of the identified plant species is determined in block 606. For example, the stage in the growth cycle may be based upon the current time of the year. The growth cycle may be defined in terms of different growth stages during the growing season at the location of the plant species. In some implementations, the growth cycle is defined by the month of the year. Months in which the plant species are dormant may not be considered. The stage of the growth cycle may also be adjusted based at least in part upon the maturity of the plant (e.g., a young plant or adult plant). The age of the plant may also be determined.

Results of the analysis of the aqueous samples, plant tissue samples, fertilizer solution (FS) samples, and/or irrigation water samples may be used in the evaluation of the availability, balances, intakes, and rate of use of the nutrients over the growth cycle of the plant 109. For example, in block 609 the analysis results of the aqueous samples may be evaluated to determine the condition of the root activity zone 112 (FIG. 1). Chemical, mineral, nutrient, ion, and/or conductivity levels of the aqueous samples may be examined and compared to predefined levels associated with the plant species. The predefined levels may define two or more ranges. The ranges may be defined for an average level of the chemical, mineral, nutrient, ion, and/or conductivity throughout the root activity zone 112 or for each depth of the root activity zone 112. For instance, the predefined levels may define a desired range based upon upper and/or lower limits. For example, the level of $NO_3^-$ and $Cl^-$ within the root activity zone 112 can be examined and compared to predefined levels associated with the plant species. Tables 1 and 6 illustrate examples of predefined levels for low, medium (or desired), and high ranges for some chemical compounds and microelements in the root activity zone 112. In other implementations, a desired level may be specified with defined upper and lower tolerances. In some cases, predefined levels may be specified for other combinations of ranges such as, e.g., very low, low, desired, high, and very high.

In addition, concentration ratios with respect to other ions, chemicals, and/or nutrients in the aqueous samples may also be determined and evaluated. For example, the level of other combinations such as, e.g., $K^+/Na^+$, $K^+/Mg^{++}$, $Ca^{++}/Na^+$, $Ca^{++}/Mg^{++}$, and/or $NO_3^-/NH_4^+$ within the root activity zone 112 may also be evaluated based upon predefined levels. Tables 2-5 illustrate examples of predefined levels for low and adequate (or desired) ranges for various ratios of ions or combinations of ions. The predefined levels for the concentrations and/or ratios may be based at least in part upon historical data and the growth patterns of the plant species. The levels (or ranges) may be varied based at least in part upon the growth cycle and/or maturity of the identified plant species. The predefined levels may change as the growth cycle moves from initial growth to producing blooms to development and ripening of the fruit. The predefined levels may also vary with the maturity of the plant. As the plant species ages, the nutritional needs of the plant changes. In addition, as the root depth changes the predefined levels may adjust for different depth levels of the root activity zone 112.

In block 612, the condition of the plant 109 may be evaluated based at least in part upon the analysis of the plant tissue samples. Plant tissue samples may be taken from, e.g., the foliage, stem, fruit, flowers, and/or roots of the plant 109 and analyzed in block 312 of FIG. 3. Chemical, mineral, nutrient, and/or conductivity levels of the plant tissue samples may be examined and compared to predefined levels associated with the plant species. Concentration ratios with respect to other ions, chemicals, and/or nutrients in the plant tissue samples may also be determined and evaluated. As described above, the predefined levels may be defined as a plurality of ranges, which may be based at least in part upon historical data and the growth cycle of the plant species. The predefined levels (or ranges) may be varied based at least in part upon where the plant tissue sample was obtained, the growth cycle, and/or maturity of the identified plant species. The growth cycle may be defined in terms of different growth stages during the growing season at the location of the plant species. In some implementations, the growth cycle is defined by the month of the year and may include months in which the plant species are dormant.

In block 615, the condition of the FS 115 (FIG. 1) is evaluated based at least in part upon the sample analysis of block 312 (FIG. 3). Chemical, mineral, nutrient, and/or conductivity levels of the FS samples may be examined and compared to predefined levels. Concentration ratios with respect to other ions, chemicals, and/or nutrients in the plant tissue samples may also be determined and evaluated. The concentrations and/or ratios may be the same or different than those evaluated for the aqueous samples. The predefined levels may define a plurality of ranges such as, e.g., a desired range based upon high and/or low level limits for some ions, chemicals, nutrients, and/or microelements in the FS 115. In other implementations, a desired level may be specified with defined upper and lower tolerances. In some cases, predefined levels may be specified for other combinations of ranges such as, e.g., very low, low, desired, high, and very high. The predefined levels (or ranges) may be varied based at least in part upon the growth cycle of the plant 109.

The interaction between the different conditions of the aqueous samples, the plant tissue samples, and/or FS samples in evaluated in block 618. As discussed with respect to FIG. 5, the utilization, absorption, and/or consumption of some ions, chemicals and nutrients may be affected by the concentration of other ions, chemicals, microelements and/or other nutrients. Different combinations of elements in the aqueous, plant tissue, and FS samples may be evaluated in block 618. Key indicators that may be used in the evaluation include the concentration ratio (CR), utilization rate (UR), and consumption index (CI) for various ions, chemicals, and/or nutrients. For example, the CR, UR, and/or CI may be determined and evaluated for one or more of anions such as, e.g., $NO_3^-$, $H_2PO_4^-$, $HCO_3^-$, $CO_3^=$, and/or $SO_4^=$; cations such as, e.g., $Ca^{++}$, $Mg^{++}$, $K^+$, and/or $NH_4^-$; and/or microelements such as, e.g., B, Fe, Mn, Cu, Zn, Mo, and/or Urea. The UR for the anions may be determined using, e.g., $Cl^-$ as the marker ion and the UR for the cations may be determined using, e.g., $Na^+$ as the marker ion. The CR, UR, and/or CI may also be determined and evaluated for one or more macronutrients such as, e.g., phosphorous and/or nitrogen based upon one or more anions and/or cations. The CR, UR, and/or CI may be compared to predefined levels defining a plurality of ranges, which may be varied based at least in part upon the growth cycle and/or maturity of the identified plant species.

Recommendations for corrective measures are then determined in block 621. The recommendations may be determined based at least in part upon the evaluations of the analyzed samples using, e.g., pattern recognition, neural network evaluation, and/or other rule based identification methods as can be appreciated. The recommendations can include, but are not limited to, changes to the chemical composition of the FS 115. The recommendations may be take into account the condition (or quality) of the irrigation water (block 624) as determined from analysis of irrigation water samples and/or the condition of the soil in the activity zone 112 (block 627), which may have been determined from the initial samples taken during the installation of the suction probes 106. Chemical, nutrient and/or ion concentrations and/or ratios of different chemicals, nutrients, or ions may be determined as described above. The recommendation may also account for the unused portion of the chemicals, nutrients, and/or ions that remain at the various depths of the root activity zone 112 and/or the portions of the chemicals, nutrients, and/or ions that are lost. Recommendation may include the current condition of the chemicals, microelements, pH, electrical conductivity, and/or other nutrients in the activity zone 112, the plant tissue, and/or the FS 115 as well as recommended corrections to return the conditions to their desired levels. The recommendations may include specified amounts of chemicals and/or nutrients to the FS 115. The addition of a specific chelating agent may also be recommended based upon the current or projected pH of the activity zone 112. In other cases, the recommendations may also include the addition of irrigation water to the FS 115 to reduce levels of certain elements. The recommendations may be based upon ion, chemical and nutrient levels throughout the root activity zone 112. In some cases, the recommendations may take into account the concentrations at different depths within the activity zone 112.

For example, current nitrogen levels may be compared to desired levels at that stage in the growth cycle to determine if adjustments may be recommended. This may include comparison of concentrations at one or more of the probe depths to determine whether the corresponding nitrogen levels need to be adjusted. Current levels in the FS 115 can also be considered in the evaluation. Key indicators such as $CR_N$, $UR_N$, and/or $CI_N$ may be determined and utilized to determine the recommendations for corrective measures to eliminate or reduce the environmental effects. The relationship between the analyzed levels and predefined levels corresponding to the plant 109 may be used to determine if the nitrogen level of the FS 115 should be adjusted by increasing or reducing the levels of, e.g., $NO_3^-$ and/or $NH_4^+$. If the nitrogen is below or above the desired range, then the current condition may be reported and recommendations may be provided to adjust the conditions. In some cases, the amount of increase or decrease in the chemicals and/or nutrients added to the FS 115 may be determined based at least in part upon the deviation from the desired range. In addition, the frequency of the addition may be provided.

Changes between the current and previous nitrogen levels in plant samples from the leaves, stalks, sap, etc., as well as variations from historical profiles over the growth cycle of the plant 109 may also be evaluated and used to determine the recommended adjustment. The interaction with other chemicals and/or nutrients and the effect on absorption and utilization by the plant 109 may also be accounted for. For instance, the relationship between the concentrations of $NO_3^-$ and $Cl^-$ can be examined to determine if the appropriate ratio exists for the plant 109. Based upon these relationships, recommendations regarding adjustments to the FS 115 may be adjusted. For example, if analysis of the aqueous and plant samples indicates that the nitrogen levels are above the predefined level in the root activity zone 112 but are below the predefined level in the plant, the recommendation may be to maintain the current nitrogen level in the FS 115 to ensure that the needs of the plant 109 are met. This recommendation may take into account the stage in the growth cycle and/or the historical profile of the plant 109, as well as current pH level and electrical conductivity.

Similar evaluations may be carried out for other ions, chemicals and/or nutrients such as, e.g., phosphorus, potassium, calcium, magnesium, ammonium, chlorides, sodium, and/or microelements such as, e.g., iron, manganese, copper, zinc, boron, and/or molybdenum. Key indicators such as CR, UR, and/or CI can be determined for one or more of these ions, chemicals and/or nutrients and utilized to determine a recommendation. The relationship between the analyzed levels and predefined levels corresponding to the plant 109 may be used to determine if the chemical and/or nutrient level of the FS 115 should be adjusted. The interaction with other chemicals and/or nutrients and the effect on absorption, utilization and consumption by the plant 109 may also be accounted for. For potassium, the relationships between the concentrations of $K^+$ and $Na^+$ and/or $K^+$ and $Mg^{++}$ can be examined to determine if the appropriate ratios exist for the plant 109. For calcium, the relationships between the concentrations of $Ca^{++}$ and $Na^+$ and/or $Ca^{++}$ and $Mg^{++}$ can be examined to determine if the appropriate ratios exist. For magnesium, the relationship between the concentrations of $Ca^{++}$ and $Mg^{++}$ can be examined to determine if the appropriate ratio exists. The recommendation of one chemical and/or nutrient may be adjusted to take into account changes in the recommendation of another chemical and/or nutrient.

If accumulation of one or more microelement(s) is detected, then an appropriate chelating agent (e.g., EDTA, DTPA, EDDHA) may be recommended, while taking into account the current and/or projected pH levels of the root activity zone 112. Adjustment to amino acids, monoammonium phosphate, monopotassium phosphate, magnesium nitrate, and/or calcium fertilizers that are provided to the plant 109 may also be recommended based upon the evaluation of the analysis information. Recommendations regarding adjustments to the irrigation patterns and/or amounts may also be recommended based upon the available information. Drainage and aeration conditions may also be evaluated.

Figure 7:
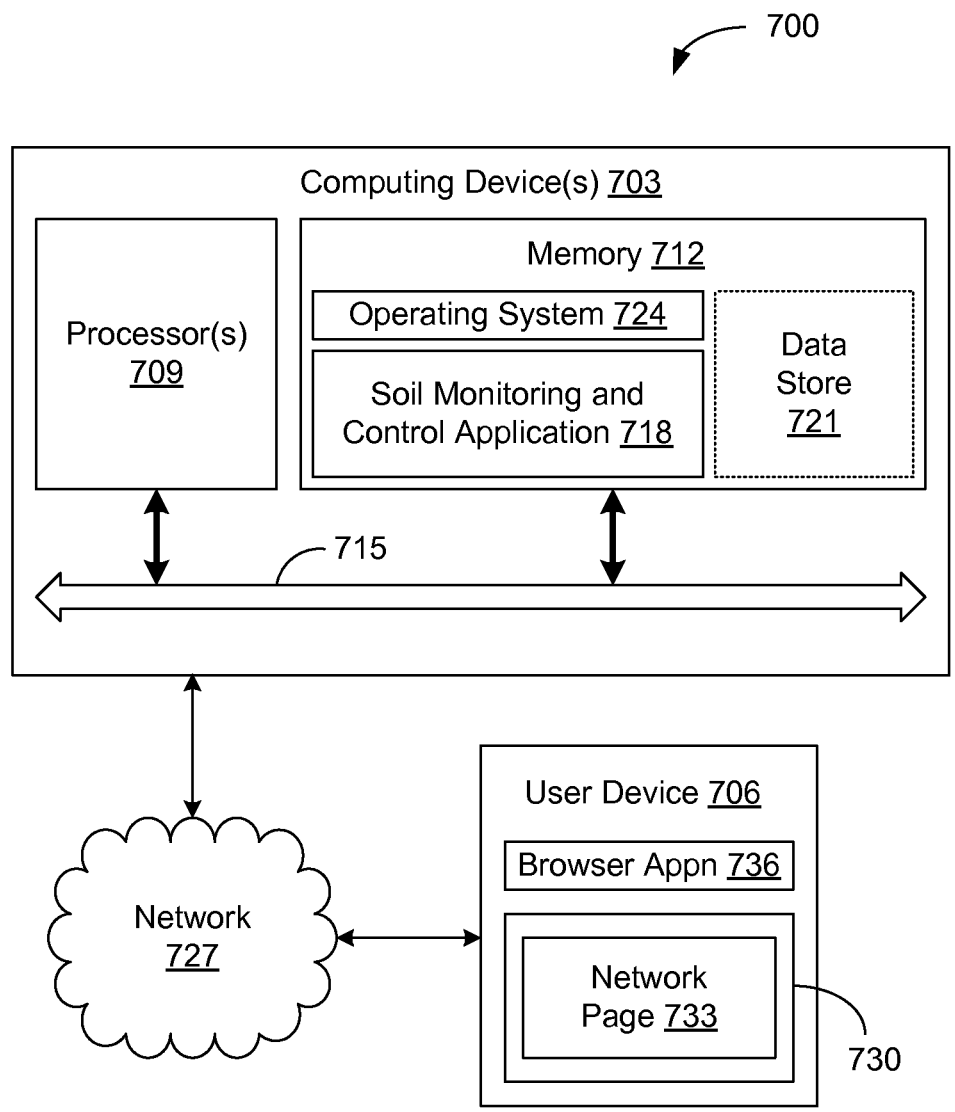
FIG. 7 is an example of a system that may be utilized in the monitoring and control of soil conditions according to various embodiments of the present disclosure.

The recommendations may also take into account the locations of the different samples within the field where the plants 109 are located. For example, adjustments to the configuration of the irrigation system may be recommended based at least in part upon differences in the chemical and/or nutrient levels at different locations within the field. Differences in the soil composition at different locations within the field may also be accounted for by recommending different fertilization solutions 115 for use in different areas of the field. In addition, corrections to the irrigation practices may be recommended such as, e.g., increasing or decreasing the irrigation cycle. In some cases, variations in weather conditions (current and/or predicted) may also be taken into account when determining the corrective recommendations. Other cultivation operations may also be recommended based at least in part upon the evaluation of the aqueous, plant tissue, and FS samples Referring now to FIG. 7, shown is an example of a system 700 that may be utilized in the monitoring and control of soil conditions. The system 700 includes one or more computing device(s) 703 and one or more user device(s) 706. The computing device 703 includes at least one processor circuit, for example, having a processor 709 and a memory 712, both of which are coupled to a local interface 715. To this end, the computing device(s) 703 may comprise, for example, a server computer or any other system providing computing capability. The computing device(s) 703 may include, for example, one or more display devices such as cathode ray tubes (CRTs), liquid crystal display (LCD) screens, gas plasma-based flat panel displays, LCD projectors, or other types of display devices, etc. The computing device(s) 703 may also include, for example various peripheral devices. In particular, the peripheral devices may include input devices such as, for example, a keyboard, keypad, touch pad, touch screen, microphone, scanner, mouse, joystick, or one or more push buttons, etc. Even though the computing device 703 is referred to in the singular, it is understood that a plurality of computing devices 703 may be employed in the various arrangements as described above. The local interface 715 may comprise, for example, a data bus with an accompanying address/control bus or other bus structure as can be appreciated.

Stored in the memory 712 are both data and several components that are executable by the processor 709. In particular, stored in the memory 712 and executable by the processor 709 are a soil monitoring and control application 718 and potentially other applications. Also stored in the memory 712 may be a data store 721 and other data. The data stored in the data store 721, for example, is associated with the operation of the various applications and/or functional entities described below. For example, the data store may include sample analysis results, corrective measures, and other data or information as can be understood. In addition, an operating system 724 may be stored in the memory 712 and executable by the processor 709. The data store 721 may be may be located in a single computing device or may be dispersed among many different devices.

The user device 706 is representative of a plurality of user devices that may be communicatively coupled to the computing device 703 through a network 727 such as, e.g., the Internet, intranets, extranets, wide area networks (WANs), local area networks (LANs), wired networks, wireless networks, networks configured for communication over a power grid, or other suitable networks, etc., or any combination of two or more such networks. In some embodiments, a user device 706 may be directly connected to the computing device 703.

The user device 706 may comprise, for example, a processor-based system such as a computer system. Such a computer system may be embodied in the form of a desktop computer, a laptop computer, a personal digital assistant, a cellular telephone, web pads, tablet computer systems, or other devices with like capability. The user device 706 includes a display device 730 upon which various network pages 733 and other content may be rendered. The user device 706 may be configured to execute various applications such as a browser application 736 and/or other applications. The browser application 736 may be executed in a user device 706, for example, to access and render network pages 733, such as web pages, or other network content served up by the computing device 703 and/or other servers. The user device 703 may be configured to execute applications beyond browser application 736 such as, for example, e-mail applications, instant message (IM) applications, and/or other applications.

The components executed on the computing device 703 include, for example, a soil monitoring and control application 718 and other systems, applications, services, processes, engines, or functionality not discussed in detail herein. The soil monitoring and control application 718 can generate network pages 733 such as web pages or other types of network content that are provided to a user device 706 in response to a request for the purpose of viewing stored data or recommended corrective measures.

It is understood that there may be other applications that are stored in the memory 712 and are executable by the processor 709 as can be appreciated. Where any component discussed herein is implemented in the form of software, any one of a number of programming languages may be employed such as, for example, C, C++, C#, Objective C, Java, Java Script, Perl, PHP, Visual Basic, Python, Ruby, Delphi, Flash, or other programming languages.

A number of software components are stored in the memory 712 and are executable by the processor 709. In this respect, the term "executable" means a program file that is in a form that can ultimately be run by the processor 709. Examples of executable programs may be, for example, a compiled program that can be translated into machine code in a format that can be loaded into a random access portion of the memory 712 and run by the processor 709, source code that may be expressed in proper format such as object code that is capable of being loaded into a random access portion of the memory 712 and executed by the processor 709, or source code that may be interpreted by another executable program to generate instructions in a random access portion of the memory 712 to be executed by the processor 709, etc. An executable program may be stored in any portion or component of the memory 712 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 712 is defined herein as including both volatile and nonvolatile memory and data storage components. Volatile components are those that do not retain data values upon loss of power. Nonvolatile components are those that retain data upon a loss of power. Thus, the memory 712 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 709 may represent multiple processors 709 and the memory 712 may represent multiple memories 712 that operate in parallel processing circuits, respectively. In such a case, the local interface 715 may be an appropriate network that facilitates communication between any two of the multiple processors 709, between any processor 709 and any of the memories 712, or between any two of the memories 712, etc. The local interface 715 may comprise additional systems designed to coordinate this communication, including, for example, performing load balancing. The processor 709 may be of electrical or of some other available construction.

Although the soil monitoring and control application 718, and other various systems described herein, may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowcharts of FIGS. 3 and 6 show the functionality and operation of an implementation of portions of a soil monitoring and control application 718. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 709 in a computer system or other system. The machine code may be converted from the source code, etc. If embodied in hardware, each block may represent a circuit or a number of interconnected circuits to implement the specified logical function(s).

Although the flowcharts of FIGS. 3 and 6 show a specific order of execution, it is understood that the order of execution may differ from that which is depicted. For example, the order of execution of two or more blocks may be scrambled relative to the order shown. Also, two or more blocks shown in succession in FIGS. 3 and/or 6 may be executed concurrently or with partial concurrence. Further, in some embodiments, one or more of the blocks shown in FIGS. 3 and/or 6 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including soil monitoring and control application 718, that comprises software or code can be embodied in any non-transitory computer-readable medium for use by or in connection with an instruction execution system such as, for example, a processor 709 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Briefly described, one embodiment, among others, comprises a method including obtaining aqueous samples extracted from a plurality of suction probes positioned at multiple depths within a soil substrate including a root activity zone of a plant species in the soil substrate; analyzing the aqueous samples to determine a chemical composition of the soil substrate; and determining amounts of an additive that is added to irrigation water supplied to the soil substrate to adjust the chemical composition of the soil substrate based at least in part upon the determined chemical composition and the plant species. At least one of the plurality of suction probes may be positioned within the root activity zone. Determining the chemical composition of the soil substrate may comprise determining a chemical composition of the root activity zone.

The method may comprise determining amounts of a plurality of additives that are added to the irrigation water supplied to the soil substrate to adjust the chemical composition of the soil substrate based at least in part upon the determined chemical composition and the plant species. The additive may comprise water, residue water, fertilizer, or any combination thereof. The method may comprise obtaining a sample of a fertilizer solution (FS) that has been supplied to the soil substrate and analyzing the FS sample to determine a composition of the FS, wherein the determined amount of additive is based at least in part upon the determined FS composition. The FS may be supplied to the soil substrate at least a predetermined time before extracting the aqueous samples from the plurality of suction probes. The sample of the FS may be collected over an entire irrigation time during which the FS is supplied to the soil substrate.

The method may comprise extracting the aqueous samples from the plurality of suction probes. A vacuum may be drawn on each of the plurality of suction probes to induce hydraulic conduction of aqueous solutions from the soil substrate into each suction probe. The method may comprise obtaining a sample of the irrigation water and analyzing the irrigation water sample to determine a composition of the irrigation water, wherein the determined amount of additive is based at least in part upon the determined irrigation water composition. The method may comprise obtaining a tissue sample of the plant species in the root activity zone and analyzing the plant tissue sample to determine a nutritional condition of the plant. The method may comprise providing the determined amounts of additive that is added to the irrigation water to produce a fertilizer solution (FS) that is supplied to the soil substrate. The method may comprise mixing the determined amounts of additive with the irrigation water to produce the FS and applying the FS to the soil substrate. The FS may be applied through a drip line.

Another embodiment, among others, comprises a method including installing a suction probe at a depth within a soil substrate; drawing a vacuum on the suction probe to induce hydraulic conduction of aqueous solutions from the soil substrate into the suction probe; extracting an aqueous sample from the suction probe after applying the vacuum for a predetermined period of time; and analyzing the aqueous sample to determine a chemical composition at the depth of the soil substrate. The method may comprise installing a plurality of suction probes at multiple depths within the soil substrate; drawing a vacuum on each of the plurality of suction probes to induce hydraulic conduction of aqueous solutions from the soil substrate into each suction probe; extracting aqueous samples from the plurality of suction probes after applying the vacuum for the predetermined period of time; and analyzing the aqueous samples to determine a chemical composition at the different depths of the soil substrate.

The aqueous samples may be analyzed to determine chemical composition at different depths of the soil substrate. At least one of the plurality of suction probes may be installed within a root activity zone of a plant species in the soil substrate. The aqueous samples may be analyzed to determine a chemical composition of the root activity zone. The method may comprise determining a corrective measure based at least in part upon the determined chemical composition of the root activity zone. The corrective measure may be a washing irrigation. The method may comprise obtaining a plurality of soil samples at different depths of the root activity zone. The method may comprise determining a corrective measure based at least in part upon the determined chemical composition of the soil substrate.

Another embodiment, among others, comprises a method including obtaining, by a computing device, a composition of a fertilizer solution (FS) that has been supplied to a soil substrate including a root activity zone of a plant species; obtaining, by the computing device, a chemical composition within the root activity zone, the chemical composition determined by analysis of an aqueous sample obtained from a suction probe positioned within the root activity zone after the FS is supplied to the soil substrate; determining, by the computing device, nutrient utilization by the plant species based at least in part upon the FS composition and the chemical composition of the root activity zone; and providing, by the computing device, an amount of additive that is added to irrigation water to produce a subsequent FS that is supplied to the soil substrate. The method may comprise obtaining the chemical composition at multiple depths within the root activity zone, the chemical composition determined by analysis of aqueous samples obtained from suction probes positioned at the multiple depths of the root activity zone after the FS is supplied to the soil substrate.

The method may comprise obtaining the chemical composition at multiple depths within the root activity zone, the chemical composition determined by analysis of aqueous samples obtained from suction probes positioned at the multiple depths of the root activity zone after the FS is supplied to the soil substrate. The method may comprise obtaining nutritional status of the plant species that is based upon analysis of a tissue sample of the plant species and determining the amounts of nutrients for the subsequent FS based at least in part upon the determined nutrient utilization and the nutritional status of the plant species. Determining nutrient utilization may include evaluating marker ion concentrations determined by analysis of the aqueous sample. Determining nutrient utilization may include determining a nitrogen utilization rate and/or a potassium utilization rate.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A method, comprising:
   obtaining aqueous samples extracted from a plurality of in situ suction probes positioned at multiple depths within a soil substrate including a root activity zone of an established plant species in the soil substrate;
   analyzing the aqueous samples to determine a chemical composition of the aqueous samples, the chemical composition comprising concentrations of a plurality of plant nutrients and non-nutrients that act as marker ions; and
   determining, via at least one computing device, nutrient utilization by the plant species based at least in part upon the concentrations and a distribution of the marker ions with respect to depth of the soil substrate; and
   determining, via the at least one computing device, amounts of an additive that is added to irrigation water applied to the soil substrate to adjust a chemical composition of the soil substrate to predefined levels, based at least in part upon the determined nutrient utilization and nutritional needs of the plant species.

2. The method of claim 1, wherein at least one of the plurality of in situ suction probes is positioned within the root activity zone.

3. The method of claim 2, wherein the chemical composition of the root activity zone of the soil substrate is modified by the irrigation water including the additive, that is applied to the soil substrate.

4. The method of claim 3, wherein the modified chemical composition of the root activity zone improves growth and production of the plant species.

5. The method of claim 1, wherein the additive comprises water.

6. The method of claim 1, wherein the additive comprises residue water.

7. The method of claim 1, wherein the additive includes fertilizer.

8. The method of claim 1, wherein determining the amounts of the additive is further based at least in part upon a composition of a fertilizer solution (FS) applied to the soil substrate before the aqueous samples are extracted from the plurality of in situ suction probes.

9. The method of claim 8, wherein the FS is applied to the soil substrate at least a predetermined time before extracting the aqueous samples from the plurality of in situ suction probes.

10. The method of claim 8, wherein a sample of the FS is collected over an entire irrigation time period during which the FS is applied to the soil substrate.

11. The method of claim 1, further comprising extracting the aqueous samples from the plurality of in situ suction probes.

12. The method of claim 11, wherein a vacuum is drawn on each of the plurality of in situ suction probes to induce hydraulic conduction of the aqueous solutions from the soil substrate into each of the plurality of in situ suction probes.

13. The method of claim 1, further comprising determining a nutritional status of the plant species based upon analysis of a tissue sample of the plant species.

14. The method of claim 1, wherein the determined amounts of the additive are added to a volume of the irrigation water to produce a fertilizer solution (FS) that is subsequently applied to the soil substrate.

15. The method of claim 8, wherein the FS is applied to the soil substrate through an irrigation system.

16. The method of claim 1, wherein analyzing the aqueous samples comprises determining the distribution of the marker ions with respect to the multiple depths within the soil substrate.

17. The method of claim 2, wherein at least one of the plurality of in situ suction probes is positioned at a depth below the root activity zone.

18. The method of claim 17, wherein determining the chemical composition of the aqueous samples comprises determining a chemical composition of at least one aqueous sample extracted from the at least one in situ section probe positioned at the depth below the root activity zone.

19. The method of claim 12, wherein the vacuum is drawn on each of the plurality of in situ suction probes for a corresponding predetermined period of time before extracting the aqueous samples.

20. The method of claim 8, wherein determining the nutrient utilization by the plant species is further based at least in part upon the composition of the FS.

21. The method of claim 13, wherein determining the amounts of the additive is further based at least in part upon the nutritional status of the plant species.

22. The method of claim 1, wherein the amounts of the additive comprise amounts of nutrients.

23. The method of claim 22, wherein the amounts of nutrients are based at least in part upon the nutrient utilization by the plant species and a nutritional status of the plant species.

24. The method of claim 1, wherein the nutrient utilization comprises at least one nutrient utilization rate.

25. The method of claim 1, wherein determining the nutrient utilization comprises determining a utilization rate of a nutrient based at least in part upon a corresponding marker ion concentration.

26. The method of claim 25, wherein determining the nutrient utilization further comprises determining absorption of water based at least in part upon a corresponding marker ion concentration.

27. The method of claim 25, wherein the utilization rate us a nitrogen utilization rate or a potassium utilization rate.

28. The method of claim 1, further comprising determining that leaching is present in the soil substrate based at least in part upon the concentrations and distribution of the marker ions.

29. The method of claim 28, wherein determining that leaching is present is further based at least in part upon electrical conductivity of the aqueous samples.

30. The method of claim 14, further comprising:
   obtaining a sample of the irrigation water; and
   analyzing the irrigation water sample to determine a composition of the irrigation water, wherein the determined amounts of the additive is based at least in part upon the determined irrigation water composition.

31. The method of claim 15, wherein the irrigation system comprises a drip line.

32. The method of claim 23, further comprising determining the nutritional status of the plant species based upon analysis of a tissue sample of the plant species.

* * * * *